Nov. 6, 1956 L. M. THOMPSON Plant Pat. 1,526
ALMOND TREE
Filed June 6, 1955
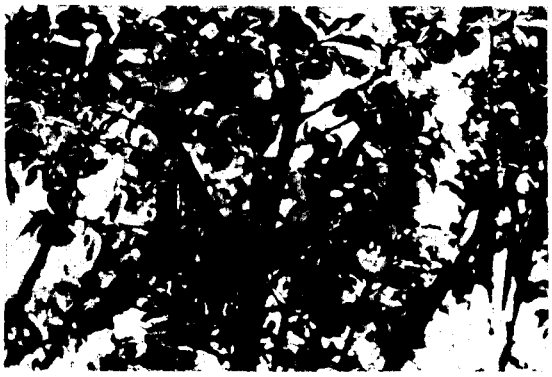
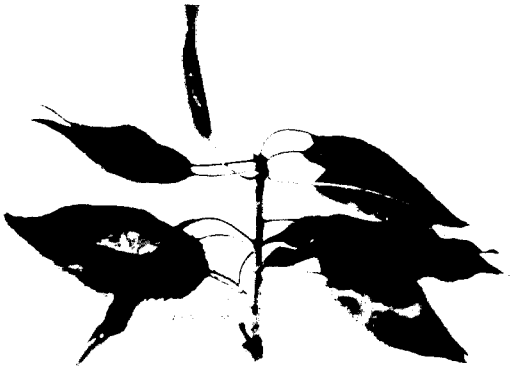
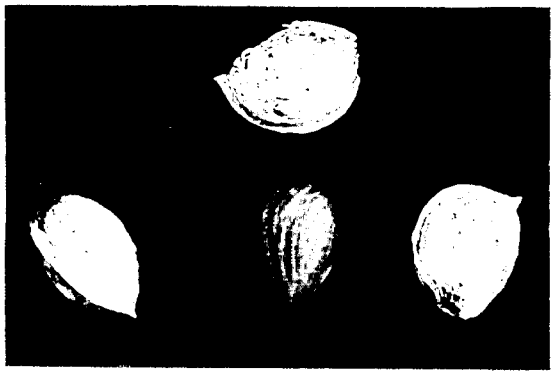
LESLIE M. THOMPSON
INVENTOR
HUEBNER, BEEHLER,
WORREL & HERZIG
ATTORNEYS
BY Richard M. Worrel United States Patent Office Plant Pat. 1,526

Patented Nov. 6, 1956

1,526

ALMOND TREE

Leslie M. Thompson, Clovis, Calif.

Application June 6, 1955, Serial No. 513,623

1 Claim. (Cl. 47—62)

The present invention relates to a new and distinct variety of almond tree, *Prunus amygdalus,* Batsch, and more particularly to such a tree similar in some respects to the unpatented Nonpareil variety but which blooms substantially later and bears markedly heavier crops.

The subject almond tree originated as a seedling which was discovered by the applicant on his ranch at 8175 East Shaw Avenue, county of Fresno and State of California. The parentage of the seedling is not definitely known but is believed to be a cross between the Nonpareil and the unpatented Texas, also known as the Mission. It germinated on the bank of a large irrigating ditch from where it was transplanted to a position adjacent to the applicant's home located in an orchard of Nonpareil and Texas varieties of almonds. The asexual reproduction of the new variety was first accomplished by the applicant in his almond orchard at the location specified by grafting into Nonpareil trees. The initial grafts have flourished and others which have subsequently been made have proved the dependability of the characteristics of the new variety by their accurate ingemination.

One of the principal problems in commercial almond production is the erratic bearing characteristics of almond trees. An orchard which bears heavily one year may have a complete crop failure the next under the same cultural conditions except for weather variations which are of course beyond the farmers' control. Although the causes of the erratic bearing of known almond varieties have been known, no satisfactory solution to the problem was known until the discovery of the subject new variety.

The blossom buds of almonds, like those of apricots, contain initials of but one blossom. If the initials of this blossom are killed, there is no alternative blossom and the bud is abscised. Even though mature trees normally bear many more blossoms than enough to bear a normal crop, late frosts frequently kill the initials and thus reduce or destroy the potential crop.

Open blossoms of almonds are generally as resistant to freezing as the blossoms of peaches. However, almond blossoms develop at much lower temperatures than peach blossoms and thus open earlier and are much more apt to reach a tender stage before the danger of frost is past. Because of this, commercial almond growing in the United States is largely limited to those areas of California where the frost hazard is at a minimum and where injury by rainy weather in spring and summer is unlikely.

The blossoming periods of almonds are also influenced by the winter chilling incurred. Almonds are recognized to possess rather short chilling requirements and even in most areas of almond culture where winters are the warmest, buds tend to open without injurious delay. However, they open somewhat earlier in the more northern latitudes of their growing zones than in the southern. It appears that chilling affects the different varieties of almonds to varying extents as to their blooming periods so that fluctuations of trees intended to have synchronous blooming periods are noted.

All commercially significant varieties of almonds grown in the United States are self-sterile. Thus, each variety must be planted adjacent to a different variety so that cross-pollinization can occur to produce the desired seed. Inasmuch as the seed is the edible part of the almond, pollinization failure is synonymous to crop failure.

Like the pollen of peaches, apricots, and most stone fruits, the almond pollen is not readily airborne and must rely for distribution upon insects that visit the blossoms. This dependence upon insects for pollen carrying purposes is also responsible for erratic bearing. Almond trees blossom early in the spring when the temperature is frequently too cool for desired insect activity. Further, the fluctuating blossoming periods for different varieties of almond trees frequently minimize or preclude the successful pollinization by insects.

The new variety of almond tree is similar to previously known commercial varieties in that it is self-sterile. It blossoms later, however, than the unpatented Nonpareil, Texas and Ne Plus Ultra. It cross pollinates excellently with the Nonpareil and Texas, with which it has been most extensively tested. Although it blossoms sufficiently later than the varieties noted to avoid most all of the hazards of late frost, the last blossoms of the earlier varieties are still on the trees when the blossoms of the new variety open so that pollinization is possible. Further, since the blossoming period is later, it occurs in warmer weather when insect activity is much more vigorous.

The subject almond is similar in many particulars to the unpatented Nonpareil but is markedly different in its later blossoming period, in its resultant more dependable bearing of regular crops, and in the size of its crops being approximately three times the average crop of the Nonpareil under similar growing conditions. When viewed from a distance, trees of the subject variety during the summer season have a somewhat rounder or drooped silhouette because of the heavy crops borne by the limbs which are caused to sag under the loads borne thereby. The leaves of the new variety are of a bright glossy green color as compared with the relatively dull green color of the Nonpareil. Further, the leaves of the instant variety are broader than those of the Nonpareil. In the nut or embryo size and in shell structure the two varieties are subtsantially identical. If there is a difference in this respect, the nut of the instant variety is somewhat thicker and more plump than the Nonpareil, and the shell may be a trifle heavier. These differences are minor, if existent. Like the Nonpareil, the shell is not always sealed completely.

In the drawing:

Fig. 1 is a colored photograph of a portion of a tree of the new variety showing characteristic fruitwood, nuts and leaves.

Fig. 2 is a colored photograph of a characteristic twig of the new variety bearing leaves arranged for convenient observation.

Fig. 3 is a colored photograph of several nuts of the subject variety, both hulled and unhulled.

Further distinguishing features of the subject almond tree over known varieties will be noted in reference to the following description in which color designations are according to the "Dictionary of Color" by Merz and Paul, second edition.

Tree generally: Large to medium size; vigorous; upright, vase-formed; very productive; and characterized by dependable regularity of crop production. Clean, no pitch boil has been observed. Grown commercially interplanted in a Nonpareil and Texas orchard on the applicant's ranch under the same cultural conditions, the new variety is found to bear approximately three times as much per acre of cured nuts as the other two varieties even during the years of maximum production by said Nonpareil and Texas varieties. During an eight year test period, the new variety bore full crops every year while the Nonpareil and the Texas bore alternately or less frequently.

Trunk: Medium caliper in relation to length, the length being approximately three times the diameter of the trunk. Surface typical for almonds generally.

Branches: Medium caliper. Smooth on new wood to medium roughness on old.

*Color.*—"Manon" Plate 6A9 to "Cameo Brown" Plate 6F9.

*Lenticels.*—Numerous to medium in number. Medium size.

Twigs during growing season:

*Color.*—Plate 15L2 with buds "Castillian Brown," Plate 719. Buds relatively closely spaced.

Leaves: Length 7½ to 9½ cm.; width 2 to 4 cm.; broader than Nonpareil; acuminate to lanceolate, medium thickness; glossy; smooth.

*Color.*—Upper surface—Bright, glossy, Plate 24C9. Lower surface—"Montecello Green," Plate 23C11. Veins—Plate 18F2.

*Margin.*—Minutely serrated.

*Petiole.*—Medium to long; medium to slender caliper.

*Glands.*—Infrequent and usually singular when occurrent.

Blossoms: Similar in form and color to Nonpareil but usually several days later to start blooming. Slightly later or concurrent with Texas.

*Color*—White to very light pink, Plate IB1 to A2.

Fruit: High quality and far more regular and heavier bearing than any other commercial varieties known to applicant. Bears while relatively young. Excellent production under climatic and other environmental conditions prevailing on applicant's farm. No tests yet conducted outside of the San Johquin Valley of California.

*Hull or involucre.*—Similar in character, color and general appearance to Nonpareil except the splitting is more dependable, hulling is easy and no, or extremely few, "stick tights" occur.

*Shell size and form.*—Small and thick. Length 2¼ cm. to 2¾ cm. Width 1½ cm. to 1⅞ cm. Thickness 1¼ cm. to 1½ cm. Medium to pronounced wing on ventral side. Dorsal side longitudinally arcuate. Small stem scar. Small pointed apex. Shell structure "paper-shell" to "soft-shell." Similar to IXL and Ne Plus Ultra, both unpatented varieties. Color—Good. Approximately Plate 9G4 to 10G6.

*Kernel.*—Single kernel per nut. No doubles yet noted. Large in relation to shell but not so large as to be unsuited to confectionary trade. Approximately 60% are of 30 per ounce size or little larger, 23% in the 30 to 34 per ounce size, and 17% in the 36 to 40 per ounce size when production is about 1½ tons per acre hulled but unshelled. Kernels represent about 60% by weight and the shells about 40% by weight of the hulled nuts. In shape, variety usually has pronounced shoulder on dorsal side near stem end.

*Pellicle.*—Thin and minutely veined. Relatively smooth. Color—Similar to Nonpareil and lighter than unpatented Drake. Plate 12F5 to Plate 12J10.

*Meat.*—White; very good quality, sweet, oily and rich but not as high flavored as the unpatented Jordan. Excellent for candy, blanching, shredding or shaving, paste, flavoring extracts and the like. Almost no gum present.

Resistance to insects and disease: Believed resistant to red spider. A specimen tree grown adjacent to an unnamed hard-shelled seedling being tested by the applicant on his farm of Nonpareil and Texas almonds, the hard-shelled seedling is constantly bothered by red spider during growing season and the Nonpareil and Texas varieties in the orchard require spraying three times a year for commercial production. The specimen tree was last sprayed in the winter of 1945 and has never shown signs of red spider or other pests or diseases.

Inasmuch as almonds are a small fruit, their picking costs are of prime importance. Hand picking from the tree is commercially impractical and even hand picking from the ground too expensive. Commercially, large canvases or other catching cloths are spread on the ground about the trunks of the trees and the trees shaken to discharge the nuts. The canvases are then gathered and the nuts poured into boxes or other containers. Nuts which have dropped too early are lost, as are those which adhere too tightly to the tree during the shaking operation. Most varieties of almonds drop many nuts voluntarily before others are sufficiently mature for harvest. This is believed to be due to uneven maturation of the nuts and/or too ready voluntary release of the nuts from the hulls. The new variety is not subject to this difficulty. Even when mature, the new variety nut clings to the tree and no significant quantity falls before harvest. At harvest time, the picking canvases are spread and the tree struck with a rubber mallet. Substantially all of the nuts of the new variety thereupon drop onto the canvas and the normally high harvesting loss is avoided.

It is expected that the described characteristics of the subject variety of almond may vary somewhat when grown under differing soil and climatic conditions but the distinctive features have proved constant in the reproduced varieties under all of the conditions this far tested. The variations incident to soil and climatic differences are no greater than those of other almonds but due to the more dependable pollenizing characteristics, the new variety has even more marked superiority where late freezing weather is a hazard than elsewhere.

Having thus described my discovery, I claim:

A new and distinct variety of almond tree, substantially as described and illustrated, characterized particularly as to novelty by its late blooming so as to avoid damage by late frost, its blooming period being substantially later than that of the Texas and Nonpareil, by its general similarity to the Nonpareil in tree appearance and growing habits, and by its markedly heavier more regular bearing than the Texas and Nonpareil.

No references cited.